United States Patent [19]

John

[11] Patent Number: 4,605,782
[45] Date of Patent: Aug. 12, 1986

[54] PROCESS FOR THE PREPARATION OF AN ALDEHYDE
[75] Inventor: Christopher S. John, Amsterdam, Netherlands
[73] Assignee: Shell Oil Company, Houston, Tex.
[21] Appl. No.: 762,647
[22] Filed: Aug. 5, 1985
[30] Foreign Application Priority Data Oct. 15, 1984 [GB] United Kingdom ................ 8426006

[51] Int. Cl.$^4$ ............................................. C07C 45/41
[52] U.S. Cl. .................................................... 568/484
[58] Field of Search ........................................ 568/484
[56] References Cited

U.S. PATENT DOCUMENTS

| 2,105,540 | 1/1938 | Lazier | 568/484 |
| 4,093,661 | 6/1978 | Trecker et al. | 568/484 |
| 4,329,512 | 5/1982 | Moy | 568/484 |
| 4,351,964 | 9/1982 | Nakamura et al. | 568/484 |
| 4,356,328 | 10/1982 | Moy | 568/484 |
| 4,521,630 | 6/1985 | Wattimena et al. | 568/484 |

FOREIGN PATENT DOCUMENTS 0101111 2/1984 European Pat. Off. ............ 568/484

Primary Examiner—Werren B. Lone

[57] ABSTRACT

An aldehyde is prepared by passing an aromatic carboxylic compound or an aliphatic carboxylic compound having at most one α-hydrogen atom in the acyl group, in the presence of hydrogen at elevated temperature over a catalyst comprising at least 25% w of iron oxide expressed as $Fe_2O_3$, calculated on the total catalyst.

13 Claims, No Drawings

PROCESS FOR THE PREPARATION OF AN ALDEHYDE

FIELD OF THE INVENTION

The invention relates to a process for the preparation of an aldehyde from a carboxylic compound, such as a carboxylic acid, ester, anhydride or salt.

BACKGROUND OF THE INVENTION

A useful method of preparing an aldehyde starting from a carboxylic acid is the so-called Rosenmund reduction in which the acid is converted into an acyl chloride which is reduced with hydrogen to the aldehyde.

In European Patent Application No. 101,111 a process for the preparation of aldehydes is described in which certain carboxylic compounds are directly hydrogenated to the corresponding aldehydes over a catalyst comprising at least one rare earth metal and at least one additional metal, e.g., iron, on a carrier. The quantity of the addition metal(s) amounts to 0.1 to 20%w and preferably 0.5 to 10%w, calculated as the element(s) and based on the weight of the carrier. The catalyst shows a rather good reactivity and a fair selectivity to the aldehydes.

However, it appeared that during the hydrogenation of a carboxylic acid over the above catalyst a considerable loss of the rare earth metal(s) took place. This loss is probably due to the formation of rare earth metal salts of the carboxylic acid to be hydrogenated and the subsequent sublimitation of the salts thus obtained.

It has now been found that iron oxide can be used as a catalyst in the preparation of aldehydes, provided that the catalyst comprises a considerable quantity of iron oxide. The presence of a rare earth metal is not required. Such a catalyst can very suitably be used in the hydrogenation of aromatic carboxylic compounds and aliphatic carboxylic compounds having at most one α-hydrogen atom in the acyl group.

SUMMARY OF THE INVENTION

The present invention therefore relates to a process for the preparation of an aldehyde from an aromatic carboxylic compound or an aliphatic carboxylic compound having at most one α-hydrogen atom in the acyl group, in which process the carboxylic compound is contacted at elevated temperature with hydrogen in the presence of a catalyst comprising at least about 25%w of iron oxide expressed as $Fe_2O_3$, calculated on the total catalyst. By an aromatic carboxylic compound is understood a compound in which the carbon atom of the carboxylic group is directly connected to a carbon atom of the atom of the aromatic moiety. In general, the aromatic moiety comprises a phenyl group, but a polynuclear aromatic group or a heterocyclic aromatic group is possible, too.

DESCRIPTION OF THE PREFERRED EMBODIMENTS

The iron oxide catalyst, as defined above, appears to show an even greater reactivity and selectivity than those described in the European Patent Application No. 101,111. Moreover, the catalyst is stable in that no catalytically active material disappears from the catalyst.

The catalyst is advantageously applied in the form of particles, the maximum dimension of which suitably lies in the range of from about 0.5 to about 15 mm. The shape of the particles is not critical; for instance, spherical, cylindrical or annular particles may be used.

The catalyst used in the process according to the invention is allowed to be free from any other catalytically active metal and may consist of iron oxide only. A catalyst containing only iron oxide shows an excellent initial reactivity and selectively. However, in course of time a deactivation occurs due to the pulverization of the catalyst particles. To avoid this pulverization, the catalyst contains a binding material. The binding material serves to retain the physical structure of the catalyst particles. The catalyst preferably comprises about 25 to about 97%w, and in particular about 50 to about 95%w of iron oxide expressed as $Fe_2O_3$, calculated on the total catalyst.

Catalysts which contain, as binding material, at least one oxide of silicon, of aluminum or of one or more transition elements tend to exhibit a very high physical stability. It is therefore preferred to employ such binding materials in catalysts used in the process according to the invention. Very suitable transition elements are chromium and molybdenum, with chromium being especially preferred.

The quantity of the binding material may vary. It is possible to use up to about 75%w of binding material, calculated on the total catalyst. In case of aluminum or silicon oxide as binding material, the quantity of aluminum or silicon oxide suitably amounts from about 25 to about 75%w of the total catalyst. It will be appreciated by those skilled in the art that a catalyst comprising about 25%w iron oxide, expressed as $Fe_2O_3$, and about 75%w aluminum or silicon oxide (carrier) represents the catalyst having the lowest iron:carrier ratio.

In catalysts which comprise at least one oxide of the transition elements, the quantity thereof preferably does not exceed about 50%w of the total catalyst. A most preferred catalyst contains about 5 to about 15%w of chromium oxide expressed as $Cr_2O_3$ calculated on the total catalyst.

The catalysts may be prepared in any conventional method. When the catalyst to be prepared should contain relatively little iron oxide, e.g. about 25–45%w, it is suitably prepared by impregnation of the binding material with a solution of an iron salt, which impregnation is optionally followed by drying and calcination. When the catalyst should contain over 45%w of iron oxide, a very suitable way of preparing the catalyst is to precipitate the hydroxides and carbonates of iron and of aluminum, silicon and/or transition elements together and to dry and calcine the composition thus obtained. Another suitable method of preparing the catalyst is to intimately mix hydroxides, oxides or salts of the above elements and optionally dry and calcine the resulting mixture.

During compacting or tabletting of the catalyst, it is sometimes advantageous to use a small amount of lubricating agent which is added to the mixture of metal oxides. The quantity of the lubricating agent depends to a large extent on the properties and effectiveness of the particular agent. A quantity of about 0.5 to about 7.5%w of lubricating agent, calculated on the total mixture of metal oxides, is suitably applied. Suitable lubricating agents are graphite, high molecular weight fatty acids (e.g. stearic, palmitic or oleic acid) and the like.

According to the present invention, carboxylic compounds which are either aromatic or aliphatic, provided they have at most one α-hydrogen atom in the acyl group, can be converted into the corresponding aldehydes. The carboxylic compounds can be selected from acids, esters, anhydrides or even salts. Aliphatic carboxylic compounds having two or more α-hydrogen atoms in the acyl group appear not to produce aldehydes in a good yield when being contacted with hydrogen over an iron oxide catalyst, but yield ketones and/or hydrocarbons instead. Ketones are formed due to decarboxylative condensation of two molecules of the carboxylic compound to be treated.

The acyl group preferably contains about 4 to about 20, in particular about 5 to about 12 carbon atoms. The acyl group may contain one or more substituents like a halogen, a hydroxy, nitro, nitroso, amino, thio, cyano or oxo group. Since a carboxylic acid is generally more readily available than the derivatives thereof, the carboxylic compound is preferably a carboxylic acid. Preferred esters which can be converted according to the invention, are $C_1-C_6$ alkyl esters of the above carboxylic acids. Preferred are benzoic acid, optionally substituted by e.g. an alkyl e.g. $C_1-C_4$ alkyl, alkoxy, e.g. $C_1-C_4$ alkoxy, hydroxy, phenoxy or halogen moiety and aliphatic acids having no α-hydrogen atoms in the acyl group, triakyl-substituted acetic acids, e.g. tri-($C_1-C_6$ alkyl)-substituted acetic acids, especially such acids containing up to 10 carbon atoms such as pivalic acid, 2-ethyl-2-methyl butanoic acid and 2,2-dimethyl pentanoic acid, being in particular preferred, since the hydrogenation of these carboxylic acids to the corresponding aldehydes according to the invention is extremely selective. A very suitable trialkyl-substituted acetic acid is pivalic acid (in which each alkyl group is a methyl group).

The actual hydrogenation reaction is preferably carried out by passing the reactants over the catalyst, either in a fixed, in a moving or in a fluidized bed. Advantageously, the process is carried out in a fixed bed. The catalyst and/or the reactants may have been preheated to a suitable reaction temperature, advantageously to at least the vaporization temperature of the carboxylic acid or the derivatives thereof, e.g. to a temperature of about 100° to about 400° C., since the carboxylic compound is preferably in the gaseous phase when being contacted with hydrogen in the presence of the catalyst. It is, however, also possible to carry out the preparation starting from liquid carboxylic compounds.

The hydrogenation can be carried out using hydrogen generated in situ, e.g. by the dehydrogenation of methanol or other alcohols, but preferably hydrogen gas or a mixture of gases containing hydrogen gas is used. In particular, the carboxylic compound is hydrogenated using hydrogen gas in a molar ratio of more than 0.1 to the said compound. Suitably, the molar ratio of hydrogen to the carboxylic compound is in the range from about 12:1 to about 0.1:1.

Preferably, the molar ratio of hydrogen to the carboxylic compound is in the range from about 4:1 to about 1:1, especially for catalysts comprising iron oxide and chromium oxide. In European Patent Application No. 101,111, only experiments are described in which the molar ratio between hydrogen and the carboxylic acid is well above 4. Since lower molar ratios can very well be applied in the process according to the present invention, a considerable advantage is obtainable over the process according to said European Patent Application as less-expensive-hydrogen is required while a similar or higher aldehyde yield is attained.

The preparation, i.e. the actual hydrogenation, is carried out at a temperature preferably ranging from about 250° to about 550° C., particularly from about about 400° to about 500° C. Advantageously, the preparation is carried out at a weight hourly space velocity of about 10 to about 10,000 kg.m.$^{-3}$h$^{-1}$, i.e. kg of carboxylic compound per m$^3$ of the catalyst bed per hour. In particular the space velocity is preferably from about 100 to about 1000 kg.m.$^{-3}$h$^{-1}$. The pressure used may be atmospheric pressure, below or above, suitably from about 0.1 to about 10 bar.

The reactants may be used per se, or diluted with an inert gas such as nitrogen or argon. Steam or water may be added to the feed to effect the hydrolysis of anhydrides into the corresponding carboxylic acids, which are subsequently reduced to the aldehydes, and to minimize the formation of carbonaceous material on the catalyst. Suitably an inert solvent is used to dissolve any solid starting materials. Toluene or benzene is very suitable.

The aldehydes prepared can find industrial application as aroma chemicals or an intermediates in the production of a broad range of chemicals.

The process will now be illustrated by the following examples which are not to be construed as limiting the invention.

EXAMPLES

In the following experiments four catalysts were used. Catalyst 1 contained 17.7%w $Fe_2O_3$ and 82.3%w $Al_2O_3$. The catalyst was prepared by impregnating γ-alumina with a solution of ferric nitrate and by drying and calcining the impregnated composition obtained. (Catalyst density: 0.930 g/ml; particle size: 14–30 mesh=0.6–1.4 mm). Catalyst 2 contained 26.3%w of $Fe_2O_3$ and 73.7%w of $Al_2O_3$ and was prepared in a similar way as catalyst 1 (catalyst density: 0.827 g/ml; particle size: 1/16" extrudate (=1.59 mm), 5–10 mm long). Catalyst 3 was prepared by compressing $Fe_2O_3$ powder, followed by crushing and sieving. Particles of 10–20 mesh (about 0.8–1.6 mm) were used. The catalyst consisted for 100%w of $Fe_2O_3$ (Catalyst density: 0.995 g/ml). Catalyst 4 was a commercially available $Fe_2O_3$-$Cr_2O_3$ composition, comprising about 86.0%w of $Fe_2O_3$, 9.7%w of $Cr_2O_3$ and 4.3%w of graphite. (Catalyst density: 1.00 g/ml; particle size: 5–10 mesh=1-.7–4.0 mm).

In all experiments the catalyst was charged to a fixed bed reactor and a mixture of a carboxylic compound and hydrogen was fed through the catalyst bed at atmospheric pressure. In experiments 1, 2 and 5–10, pivalic acid was fed to the reactor in a toluene solution in which the pivalic acid/toluene molar ratio was 1.0:0.3. Further reaction conditions are indicated in more detail hereinafter.

EXAMPLE I

The reduction of pivalic acid to pivalaldehyde was performed using catalysts having different iron oxide content. Conditions and results are indicated in Table I.

TABLE I

| Exp. No. | Catalyst No. | T °C. | H$_2$/acid mol/mol | WHSV kg·m$^{-3}$·h$^{-1}$ | Conversion | Selectivity mol % |
|---|---|---|---|---|---|---|
| 1 | 1 | 420 | 5.6 | 302 | 66 | 88 |
| 2 | 2 | 420 | 5.0 | 480 | 74 | 99 |

TABLE I-continued

| Exp. No. | Catalyst No. | T °C. | H$_2$/acid mol/mol | WHSV kg·m$^{-3}$·h$^{-1}$ | Conversion | Selectivity mol % |
|---|---|---|---|---|---|---|
| 3 | 3 | 430 | 4.2 | 397 | 88 | 78 |
| 4 | 4 | 427 | 3.3 | 982 | 84 | 98 |

The results of the above experiments clearly show that the catalysts 2-4 are more active than catalyst 1, showing a higher conversion at higher space velocities and lower H$_2$/acid molar ratios. Catalyst 4 (Fe$_2$O$_3$-Cr$_2$O$_3$ composition) apparently is the best catalyst showing an excellent conversion and selectivity at the highest space velocity and lowest H$_2$/acid ratio.

EXAMPLE II

The experiments were run with catalyst 2 and 4 at various H$_2$/acid ratios and space velocities, as indicated in Table II.

TABLE

| Exp. No. | Catalyst No. | T °C. | H$_2$/acid mol/mol | WHSV kg·m$^{-3}$·h$^{-1}$ | Conversion | Selectivity mol % |
|---|---|---|---|---|---|---|
| 5 | 2 | 425 | 2.5 | 479 | 49 | 98 |
| 6 | 2 | 420 | 2.5 | 959 | 37 | 97 |
| 7 | 2 | 420 | 5.2 | 227 | 94 | 97 |
| 8 | 2 | 444 | 5.0 | 480 | 86 | 97 |
| 9 | 2 | 420 | 10.0 | 226 | 97 | 97 |
| 10 | 2 | 445 | 9.8 | 481 | 97 | 95 |
| 11 | 4 | 435 | 2.1 | 506 | 86 | 99 |
| 12 | 4 | 435 | 2.0 | 808 | 79 | 98 |
| 13 | 4 | 435 | 1.9 | 1635 | 64 | 100 |
| 14 | 4 | 430 | 3.6 | 471 | 94 | 94 |
| 15 | 4 | 435 | 3.4 | 722 | 92 | 96 |
| 16 | 4 | 430 | 4.5 | 380 | 96 | 95 |

From the results, it is apparent that for both catalysts an increased aldehyde yield can be obtained by increasing the H$_2$/acid ratio or decreasing the space velocity. It is also evident that for optimal performance a lower H$_2$/acid molar ratio may be applied with catalyst 4 than with catalyst 2. Additionally, higher space velocities can be dealt with, using catalyst 4.

EXAMPLE III

The reduction of several carboxylic acids and two esters was carried out using catalyst 2 or 4 as illustrated in Table III.

TABLE III

| Experiment No. | Catalyst No. | Acid or Ester | T °C. | H$_2$/acid or ester mol/mol | WHSV kg·m$^{-3}$·h$^{-1}$ | Conversion % | Selectivity mol. % |
|---|---|---|---|---|---|---|---|
| 17 | 2 | 2-ethyl-2-methyl butanoic acid | 430 | 12.3 | 248 | 86 | 75 |
| 18 | 4 | 2-ethyl-2-methyl butanoic acid | 435 | 2.8 | 449 | 90 | 92 |
| 19 | 4 | 2-ethyl-2-methyl butanoic acid | 435 | 3.0 | 827 | 90 | 92 |
| 20 | 2 | 2,2-dimethyl-pentanoic acid | 440 | 8.4 | 365 | 91 | 71 |
| 21 | 4 | 2,2-dimethyl-pentanoic acid | 424 | 3.8 | 635 | 93 | 82 |
| 22 | 2 | benzoic acid | 450 | 3.9 | 172 | 94 | 75 |
| 23 | 4 | benzoic acid | 420 | 4.0 | 160 | 80 | 90 |
| 24 | 2 | methyl benzoate | 420 | 10.1 | 272 | 77 | 88 |
| 25 | 4 | p-t-butyl-benzoic acid | 435 | 2.8 | 224 | 100 | 95 |
| 26 | 4 | m-phenoxybenzoic acid | 420 | 4.0 | 115 | 100 | 41 |
| 27 | 2 | methyl m-phenoxy benzoate | 400 | 4.0 | 120 | 90 | 70 |
| 28 | 4 | "Versatic 10" (') | 386 | 3.4 | 634 | 80 | 91 |

(') "Versatic 10" is a registered trade mark for a mixture of saturated mono-carboxylic acids having 10 carbon atoms per molecule, and wherein the carboxyl group is attached to a tertiary or quaternary carbon atom.

The results of experiments 17-28 show that the process according to the present invention can very well be applied to a variety of carboxylic compounds. Comparison of the results of experiments 18 and 19 shows that catalyst 4 is excellent even when the space velocity is increased.

What is claimed is:

1. A process for the preparation of an aldehyde from an aromatic carboxylic acid or an aliphatic carboxylic acid having at most one α-hydrogen atom in the acyl group, which process comprises contacting the carboxylic acid at elevated temperature with hydrogen in the presence of a catalyst consisting essentially of at least 25%w of iron oxide expressed as Fe$_2$O$_3$, calculated on the total catalyst, with the remainder being binding materials.

2. The process according to claim 1 wherein the catalyst contains a binding material.

3. The process of claim 1 wherein the catalyst comprises 50 to 95%w of iron oxide, expressed as Fe$_2$O$_3$ calculated on the total catalyst.

4. The process of claim 1 wherein the catalyst contains at least one oxide of silicon, of aluminum or of one or more transition elements.

5. The process of claim 4 wherein the catalyst contains chromium oxide and/or molybdenum oxide.

6. The process of claim 5 wherein the catalyst contains 5 to 15%w of chromium oxide, expressed as Cr$_2$O$_3$ calculated on the total catlayst.

7. The process of claim 1 wherein the carboxylic acid is benzoic acid, a substituted benzoic acid or an aliphatic carboxylic acid having no α-hydrogen atoms in the acyl group.

8. The process of claim 7 wherein the carboxylic acid is a trialkyl substituted acetic acid.

9. The process of claim 8 wherein the carboxylic acid is pivalic acid.

10. The process of claim 1 wherein the carboxylic compound is in the gaseous phase when being contacted with hydrogen in the presence of the catalyst.

11. The process of claim 1 wherein the molar ratio of hydrogen to the carboxylic compound is in the range form 12:1 to 0.1:1.

12. The process of claim 11 wherein the molar ratio of hydrogen to the carboxylic compound is in the range from 4:1 to 1:1.

13. The process of claim 1 wherein the temperature is in the range of from 250° to 550° C., the pressure is in the range of form 0.1 to 10 bar and the weight hourly space velocity of the carboxylic compound is in the range of from 10 to 10,000 kg.m.$^{-3}$h$^{-1}$.

* * * * *